(12) United States Patent
Song

(10) Patent No.: US 11,773,073 B2
(45) Date of Patent: Oct. 3, 2023

(54) METHOD FOR SYNTHESIZING MYRICETIN

(71) Applicant: SHANGHAI YIN SHENG CONSULTING CORPORATION (LIMITED LIABILITY PARTNERSHIP), Shanghai (CN)

(72) Inventor: Kunyuan Song, Shanghai (CN)

(73) Assignee: SHANGHAI YINSHENG CONSULTING CORPORATION (LIMITED LIABILITY PARTNERSHIP), Shanghai (CN)

( * ) Notice: Subject to any disclaimer, the term of this patent is extended or adjusted under 35 U.S.C. 154(b) by 239 days.

(21) Appl. No.: 17/428,919

(22) PCT Filed: May 8, 2020

(86) PCT No.: PCT/CN2020/089150
§ 371 (c)(1),
(2) Date: Aug. 5, 2021

(87) PCT Pub. No.: WO2021/068501
PCT Pub. Date: Apr. 15, 2021

(65) Prior Publication Data
US 2022/0073486 A1 Mar. 10, 2022

(30) Foreign Application Priority Data

Oct. 12, 2019 (CN) .......................... 201910967198.3

(51) Int. Cl.
C07D 311/30 (2006.01)
(52) U.S. Cl.
CPC .................. C07D 311/30 (2013.01)

(58) Field of Classification Search
CPC .................................................. C07D 311/30
See application file for complete search history.

(56) References Cited

FOREIGN PATENT DOCUMENTS

| CN | 103275049 A | 9/2013 |
|---|---|---|
| CN | 105294630 A | 2/2016 |
| CN | 108586409 A | 9/2018 |
| CN | 110627761 A | 12/2019 |

Primary Examiner — Golam M Shameem
(74) Attorney, Agent, or Firm — Muncy, Geissler, Olds & Lowe, P.C.

(57) ABSTRACT

This application discloses a method for synthesizing myricetin, which includes the following steps: adding an alkaline solution to an aqueous solution of dihydromyricetin, and heating under a reflux state after the addition; adding an aqueous solution of selenium dioxide, stirring at a reflux temperature after the addition, and cooling to room temperature after the reaction is complete; adding acid to adjust pH, stirring, rotary evaporation, stirring, and filtering; adding an aqueous solution of ethanol to a filter cake to make a slurry, filtering, washing the filter cake with the aqueous solution of ethanol, collecting the filter cake and drying to obtain red selenium; combining organic phases, spin-drying until there is no ethanol smell, precipitating a large amount of solids, filtering, and washing the filter cake with the aqueous solution of ethanol to obtain a yellow solid which is myricetin. The advantages of the disclosure are: 1. simple and easy to operate the reaction; 2. mainly using water and a small amount of ethanol as solvents so that the three wastes are less discharged; 3. recovering red selenium which is economically valuable; 4. obtaining myricetin of high purity; 5. serving multiple purposes with good economic benefits, and suitable for scale-up production.

10 Claims, No Drawings

METHOD FOR SYNTHESIZING MYRICETIN

BACKGROUND OF THE INVENTION

Technical Field of the Invention

This application relates to the field of pharmacy technology, in particular to a method for synthesizing myricetin.

Background

Myricetin, which has a molecular formula as $C_{15}H_{10}O_8$ and a chemical name as 3,5,7-trihydroxy-2-(3,4,5-hexahydroxyphenyl)-4H-1-benzopyran-4-one, is a flavonol compound widely found in bayberry and other natural plants. It has various pharmacological activities such as anti-inflammatory and analgesic, anti-tumor, lowering blood sugar, protecting liver and so on, showing abundant resource advantages and huge potential utilization value.

At present, the synthetic methods of myricetin are mainly divided into the following types: natural extraction, sodium hydroxide-hydrogen peroxide system oxidation method, sodium hypochlorite-aluminum chloride/ferric chloride oxidation method, and chemical synthesis method using mesitylene as starting material.

The content of myricetin in natural plants is extremely low, hard for extraction and enrichment, low yield, difficult to meet the requirements of the purity of product, and high cost; the sodium hydroxide-hydrogen peroxide oxidation method to directly oxidizes dihydromyricetin to semi-synthesize myricetin makes the yield of only 15-20% and the reaction process difficult to control, the post-treatment is cumbersome, and not suitable for scale-up production; the oxidation of sodium hypochlorite-aluminum trichloride/ferric chloride makes a lot of waste water and waste residue resulting in pollution of the environment, and not suitable for scale-up production; synthesizing myricetin with mesitylene as the starting material takes a high cost of raw materials and intermediates, and makes a large amount of organic waste liquid, low yield, and not suitable for scale-up production.

SUMMARY OF INVENTION

This application provides a semi-synthetic method of myricetin, which utilizes dihydromyricetin extracted from natural extracts to produce synthetic myricetin on a large scale. The yield is significantly improved and the cost is greatly reduced, which is suitable for industrialized production.

This application adopts the following technical solutions:

A method for synthesizing myricetin, which includes the following steps:

(1) adding an alkaline solution to an aqueous solution of dihydromyricetin, and heating under a reflux state after the addition;

(2) adding an aqueous solution of selenium dioxide, stirring at a reflux temperature after the addition, and cooling to room temperature after the reaction is complete;

(3) adding acid to adjust pH, stirring, rotary evaporation, stirring, and filtering;

(4) adding an aqueous solution of ethanol to a filter cake to make a slurry, filtering, washing the filter cake with the aqueous solution of ethanol, collecting the filter cake and drying to obtain red selenium;

(5) combining organic phases, spin-drying until there is no ethanol smell, precipitating a large amount of solid, filtering, and washing the filter cake with the aqueous solution of ethanol to obtain a yellow solid which is myricetin.

Further, the alkaline solution includes, but is not limited to, an aqueous solution of sodium hydroxide, an aqueous solution of potassium hydroxide, an aqueous solution of potassium tert-butoxide, and an aqueous solution of sodium tert-butoxide.

Further, the mass ratio of the alkaline solution to the dihydromyricetin is 1:3-6.

Further, in step (1), the step of heating is for 10-30 minutes.

Further, the mass ratio of selenium dioxide to dihydromyricetin is 1:1-6.

Further, in step (2), the step of stirring is performed for 1-2 hours.

Further, the acidic solution includes, but is not limited to, hydrochloric acid, glacial acetic acid, dilute sulfuric acid, and hydrobromic acid.

Further, in step (3), the rotary evaporation makes the volume of the acidic solution 3 to 5 times the volume of the dihydromyricetin.

Further, in step (4), the aqueous solution of ethanol is an 80% ethanol aqueous solution.

Further, in step (5), the aqueous solution of ethanol is a 10% ethanol aqueous solution.

The technical solution adopted in this application is using dihydromyricetin as a raw material, water as a solvent, and performing oxidization to form myricetin under the action of selenium dioxide and alkaline solution. Compared with other processes, it has the following beneficial effects:

1. simple and easy to operate the reaction;
2. mainly using water and a small amount of ethanol as solvents so that the three wastes are less discharged;
3. recovering red selenium which is economically valuable;
4. obtaining myricetin of high purity;
5. serving multiple purposes with good economic benefits, and suitable for scale-up production.

DETAILED DESCRIPTION OF THE INVENTION

In order to make the purpose, technical solutions and advantages of the present application clearer, the technical solutions of the present application will be described clearly and completely in conjunction with specific embodiments of the present application. Obviously, the described embodiments are only a part of the embodiments of the present application, rather than all the embodiments. Based on the embodiments in this application, all other embodiments obtained by those of ordinary skill in the art without creative work shall fall within the protection scope of this application.

Example 1

(1) Dihydromyricetin (45 g) was dissolved in 300 ml of deionized water, then heated to reflux to be dissolved into clear solution, and aqueous solution (40 ml) of sodium hydroxide (10 g) was slowly added and heated for 15 minutes in a reflux state after the addition.

(2) Aqueous solution (60 ml) of selenium dioxide (15 g) was slowly added dropwise and stirred at reflux temperature for 90 minutes after the addition, and slowly cooled to 20-30° C. after the reaction is completed.

(3) 5M hydrochloric acid was added to adjust the pH to 4~5, stirred for 30 minutes, gone through rotate evaporation until its volume changing to 3~5 times the volume of dihydromyricetin, stirred at 10~20° C. for 2~3 hours, and filtered.

(4) Ethanol aqueous solution (80%, 200 ml) was added into a filter cake for 1~2 hours to make a slurry, filtered, and the filter cake wash washed with the ethanol aqueous solution, the filter cake was collected and dried to obtain red selenium elemental solid, the yield 95%, and the purity was greater than 99%.

(5) The organic phases are combined, and spin-dried until there is no ethanol smell, a large amount of solid was precipitated, filtered, aid the filter cake was washed with ethanol aqueous solution (10%) to obtain 19 grams of yellow solid, which was myricetin, the yield: 42%, and the purity was greater than 95%.

Example 2

(1) Dihydromyricetin (60 g) was dissolved in 500 ml of deionized water, then heated to reflux to be dissolved into clear solution, and aqueous solution (40 ml) of sodium hydroxide (10 g) was slowly added and heated for 10 minutes in a reflux state after the addition.

(2) Aqueous solution (60 ml) of selenium dioxide (10 g) was slowly added dropwise and stirred at reflux temperature for 90 minutes after the addition, and slowly cooled to 20-30° C. after the reaction is completed.

(3) Dilute sulfuric acid was added to adjust the pH to 4~5, stirred for 30 minutes, gone through rotate evaporation until its volume changing to 3~5 times the volume of dihydromyricetin, stirred at 10~20° C. for 2~3 hours, and filtered.

(4) Ethanol aqueous solution (80%) was added into a filter cake for 1~2 hours to make a slurry, filtered, and the filter cake wash washed with the ethanol aqueous solution, the filter cake was collected and dried to obtain red selenium elemental solid.

(5) The organic phases are combined, and spin-dried until there is no ethanol smell, a large amount of solid was precipitated, filtered, and the filter cake was washed with ethanol aqueous solution (10%) to obtain yellow solid, which was myricetin.

Example 3

(1) Dihydromyricetin (60 g) was dissolved in 500 ml of deionized water, then heated to reflux to be dissolved into clear solution, and aqueous solution (100 ml) of sodium hydroxide (15 g) was slowly added and heated for 30 minutes in a reflux state after the addition.

(2) Aqueous solution (120 ml) of selenium dioxide (30 g) was slowly added dropwise and stirred at reflux temperature for 120 minutes after the addition, and slowly cooled to 20-30° C. after the reaction is completed.

(3) Glacial acetic acid was added to adjust the pH to 4~5, stirred for 30 minutes, gone through rotate evaporation until its volume changing to 3~5 times the volume of dihydromyricetin, stirred at 10~20° C. for 2~3 hours, and filtered.

(4) Ethanol aqueous solution (80%) was added into a filter cake for 1~2 hours to make a slurry, filtered, and the filter cake wash washed with the ethanol aqueous solution, the filter cake was collected and dried to obtain red selenium elemental solid.

(5) The organic phases are combined, and spin-dried until there is no ethanol smell, a large amount of solid was precipitated, filtered, and the filter cake was washed with ethanol aqueous solution (10%) to obtain yellow solid, which was myricetin.

Example 4

(1) Dihydromyricetin (45 g) was dissolved in 300 ml of deionized water, then heated to reflux to be dissolved into clear solution, and aqueous solution (100 ml) of sodium hydroxide (20 g) was slowly added and heated for 30 minutes in a reflux state after the addition.

(2) Aqueous solution (180 ml) of selenium dioxide (45 g) was slowly added dropwise and stirred at reflux temperature for 120 minutes after the addition, and slowly cooled to 20-30° C. after the reaction is completed.

(3) Dilute sulfuric acid was added to adjust the pH to 4~5, stirred for 30 minutes, gone through rotate evaporation until its volume changing to 3~5 times the volume of dihydromyricetin, stirred at 10~20° C. for 2~3 hours, and filtered.

(4) Ethanol aqueous solution (80%) was added into a filter cake for 1~2 hours to make a slurry, filtered, and the filter cake wash washed with the ethanol aqueous solution, the filter cake was collected and dried to obtain red selenium elemental solid.

(5) The organic phases are combined, and spin-dried until there is no ethanol smell, a large amount of solid was precipitated, filtered, and the filter cake was washed with ethanol aqueous solution (10%) to obtain yellow solid, which was myricetin.

The above descriptions are only examples of the present application, and are not used to limit the present application. For those skilled in the art, this application can have various modifications and changes. Any modification, equivalent replacement, improvement, etc. made within the spirit and principle of this application shall be included in the scope of the claims of this application.

The invention claimed is:
1. A synthetic method of myricetin, comprises the following steps:
   (1) adding an alkaline solution to an aqueous solution of dihydromyricetin, and heating under a reflux state after the addition;
   (2) adding an aqueous solution of selenium dioxide, stirring at a reflux temperature after the addition, and cooling to room temperature after the reaction is complete;
   (3) adding acidic solution to adjust pH to 4~5, stirring, rotary evaporation, stirring at 10~20° C. for 2~3 hours, and filtering;
   (4) adding an aqueous solution of ethanol to a filter cake to make a slurry, filtering, washing the filter cake with the aqueous solution of ethanol, collecting the filter cake and drying to obtain red selenium;
   (5) combining organic phases, spin-drying until there is no ethanol smell, precipitating a large amount of solid, filtering, and washing the filter cake with the aqueous solution of ethanol to obtain a yellow solid which is myricetin.
2. The method according to claim 1, wherein the alkaline solution is one or more of an aqueous solution of sodium hydroxide, an aqueous solution of potassium hydroxide, an aqueous solution of potassium tert-butoxide, and an aqueous solution of sodium tert-butoxide.

3. The method according to claim 1, wherein the mass ratio of the alkaline solution to the dihydromyricetin is 1:3-6.

4. The method according to claim 1, wherein in step (1) the step of heating is for 10-30 minutes.

5. The method according to claim 1, wherein the mass ratio of selenium dioxide to dihydromyricetin is 1:1-6.

6. The method according to claim 1, wherein in step (2) the step of stirring is performed for 1-2 hours.

7. The method according to claim 1, wherein the acidic solution includes, hydrochloric acid, glacial acetic acid, dilute sulfuric acid, and hydrobromic acid.

8. The method according to claim 1, wherein in step (3) the rotary evaporation makes the volume of the acidic solution 3~5 times the volume of the dihydromyricetin.

9. The method according to claim 1, wherein in step (4) the aqueous solution of ethanol is an 80% ethanol aqueous solution.

10. The method according to claim 1, wherein in step (5) the aqueous solution of ethanol is a 10% ethanol aqueous solution.

\* \* \* \* \*